United States Patent [19]

Rosenberg et al.

[11] Patent Number: 4,977,277
[45] Date of Patent: Dec. 11, 1990

[54] FUNCTIONALIZED PEPTIDYL AMINODIOLS AND -TRIOLS 4-AMINO-5-CYCLOHEXYL-3-HYDROXY-1,2-OXOPENTANE AND DERIVATIVES THEREOF

[75] Inventors: Saul H. Rosenberg; Jay R. Luly; Jacob J. Plattner, all of Libertyville, Ill.

[73] Assignee: Abbott Laboratories, Abbott Park, Ill.

[21] Appl. No.: 361,522

[22] Filed: Jun. 5, 1989

Related U.S. Application Data

[60] Division of Ser. No. 191,714, May 9, 1988, Pat. No.

[51] Int. Cl.$^5$ .................. C07F 7/10; C07D 303/36
[52] U.S. Cl. .................... 549/215; 549/551
[58] Field of Search .................. 549/551, 215

[56] References Cited

FOREIGN PATENT DOCUMENTS 0230266 7/1987 European Pat. Off. .
0309766 4/1989 European Pat. Off. .

OTHER PUBLICATIONS

Luby, R. et al., "Peptidylaminodiols", CA 105: 191618b, (1986).

Primary Examiner—Robert T. Bond
Assistant Examiner—Amelia A. Owens
Attorney, Agent, or Firm—Steven R. Crowley; Steven F. Weinstock

[57] ABSTRACT

The invention relates to renin inhibiting compounds of the formula

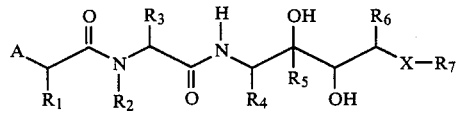

wherein A is hydrogen; loweralkyl; arylalkyl; OR$_8$ or SR$_8$ wherein R$_8$ is hydrogen, loweralkyl or aminoalkyl; NR$_9$R$_{10}$ wherein R$_9$ and R$_{10}$ are independently selected from hydrogen, loweralkyl, aminoalkyl, cyanoalkyl and hydroxyalkyl;

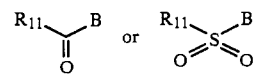

wherein B is NH, alkylamino, S, O, CH$_2$ or CHOH and R$_{11}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, carboxylic acid-substituted alkyl, alkoxycarbonylalkyl, aminoalkyl, N-protected aminoalkyl, alkylaminoalkyl, dialkylaminoalkyl, (N-protected)-(alkyl)aminoalkyl, (heterocyclic)alkyl or a substituted or unsubstituted heterocyclic; R$_1$ is loweralkyl, cycloalkylmethyl, benzyl, α-methylbenzyl, α,α-dimethylbenzyl, 4-methoxybenzyl, halobenzyl, (1-naphthyl)methyl, (2-naphthyl)methyl, (4-imidazoyl)methyl, phenethyl, phenoxy, thiophenoxy or anilino; provided if R$_1$ is phenoxy, thiophenoxy or anilino, B is CH$_2$ or CHOH or A is hydrogen; R$_3$ is loweralkyl, benzyl or heterocyclic ring-substituted methyl; R$_4$ is lower-alkyl, cycloalkyl- methyl or benzyl; R$_2$, R$_5$ and R$_6$ are independently hydrogen or loweralkyl; X is O, NH or S; R$_7$ is hydrogen, loweralkyl, alkanoyl, alkylsulfonyl

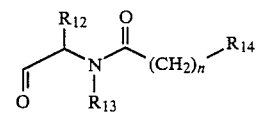

wherein R$_{12}$ and R$_{13}$ are independently hydrogen or loweralkyl, n is 0–2 and R$_{14}$ is substituted or unsubstituted phenyl or heterocyclic; or XR$_7$ together are loweralkylsulfonyl, N$_3$ or Cl, and pharmaceutically acceptable salts thereof.

6 Claims, No Drawings

FUNCTIONALIZED PEPTIDYL AMINODIOLS AND -TRIOLS 4-AMINO-5-CYCLOHEXYL-3-HYDROXY-1,2-OXO-PENTANE AND DERIVATIVES THEREOF

TECHNICAL FIELD

This is a division of U.S. patent application Ser. No. 191,714, filed May 9, 1988, which is a continuation of U.S. patent application Ser. No. 943,566, filed Dec. 31, 1986, which is a continuation in part of U.S. patent application Ser. No. 818,715, filed Jan. 16, 1986, which is a continuation in part of U.S. patent application Ser. No. 693,951, filed Jan. 23, 1985.

The present invention relates to novel organic compounds which inhibit renin, processes for making such compounds, synthetic intermediates employed in these processes and method of treating hypertension with such compounds.

BACKGROUND ART

Renin is a proteolytic enzyme synthesized and stored principally in a specific part of the kidney called the juxtaglomerular apparatus. Any of three different physiologic circumstances may cause the release of renin into the circulation: (a) a decrease in the blood pressure entering or within the kidney itself; (b) a decrease in the blood volume in the body; or (c) a fall in the concentration of sodium in the distal tubules of the kidney.

When renin is released into the blood from the kidney, the renin-angiotensin system is activated, leading to vasoconstriction and conservation of sodium, both of which result in increased blood pressure. The renin acts on a circulating protein, angiotensinogen, to cleave out a fragment called angiotensin I (AI). AI itself has only slight pharmacologic activity but, after additional cleavage by a second enzyme, angiotensin converting enzyme (ACE), forms the potent molecule angiotensin II (AII). The major pharmacological effects of AII are vasoconstriction and stimulation of the adrenal cortex to release aldosterone, a hormone which causes sodium retention. AII is cleaved by an aminopeptidase to form angiotensin III (AIII), which, compared to AII, is a less potent vasoconstrictor but a more potent inducer of aldosterone release.

Inhibitors of renin have been sought as agents for control of hypertension and as diagnostic agents for identification of cases of hypertension due to renin excess.

With these objectives in mind, the renin-angiotensin system has been modulated or manipulated, in the past, with ACE inhibitors. However, ACE acts on several substrates other than angiotensin I (AI), most notably the kinins which cause such undesirable side effects as pain, "leaky" capillaries, prostaglandin release and a variety of behavioral and neurologic effects. Further, ACE inhibition leads to the accumulation of AI. Although AI has much less vasoconstrictor activity than AII, its presence may negate some of the hypotensive effects of the blockade of AII synthesis.

Inhibition of other targets in the renin angiotensin system such as AII with compounds such as saralasin can block AII activity, but would leave unimpaired and perhaps enhance the hypertensive effects of AIII.

On the other hand, there are no known side effects which result when renin is inhibited from acting on its substrate. Considerable research efforts have thus been carried out to develop useful inhibitors of renin. Past research efforts have been directed to renin antibodies, pepstatin, phospholipids and substrate analogs such as tetrapeptides and octapeptides to tridecapeptides. These inhibitors either demonstrate poor activity in inhibiting renin production or poor specificity for inhibiting renin only. However, Boger et al. have reported that statine-containing peptides possess potent and specific renin-inhibiting activity (Nature, Vol. 303, p. 81, 1983). In addition, Szelke and co workers have described polypeptide analogs containing a non peptide link (Nature, Vol. 299, p. 555, 1982) which also cause potent renin inhibition and show a high specificity for this enzyme.

DISCLOSURE OF THE INVENTION

In accordance with the present invention, there are renin inhibiting compounds of the formula:

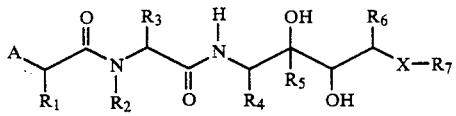

wherein A is hydrogen; loweralkyl; arylalkyl; $OR_8$ or $SR_8$ wherein $R_8$ is hydrogen, loweralkyl or amino alkyl; $NR_9R_{10}$ wherein $R_9$ and $R_{10}$ are independently selected from hydrogen, loweralkyl, aminoalkyl, cyanoalkyl and hydroxyalkyl;

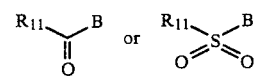

wherein B is NH, alkylamino, S, O, $CH_2$ or CHOH and $R_{11}$ is loweralkyl, cycloalkyl, aryl, arylalkyl, alkoxy, alkenyloxy, hydroxyalkoxy, dihydroxyalkoxy, arylalkoxy, arylalkoxyalkyl, amino, alkylamino, dialkylamino, (hydroxyalkyl)(alkyl)amino, (dihydroxyalkyl)(alkyl)amino, carboxylic acid substituted alkyl, alkoxycarbonylalkyl, aminoalkyl, N-protected aminoalkyl, alkylaminoalkyl, dialkylaminoalkyl, (N-protected)-(alkyl)aminoalkyl, (heterocyclic)alkyl or a substituted or unsubstituted heterocyclic; $R_1$ is loweralkyl, cycloalkylmethyl, benzyl, α-methylbenzyl, α,α-dimethylbenzyl, 4-methoxybenzyl, halobenzyl, (1-naphthyl)-methyl, (2-naphthyl)methyl, (4-imidazolyl)methyl, phenethyl, phenoxy, thiophenoxy or anilino; provided if $R_1$ is phenoxy, thiophenoxy or anilino, B is $CH_2$ or CHOH or A is hydrogen; $R_3$ is loweralkyl, benzyl or heterocyclic ring substituted methyl; $R_4$ is loweralkyl, cycloalkyl- methyl or benzyl; $R_2$, $R_5$ and $R_6$ are independently hydrogen or loweralkyl; X is O, NH or S; $R_7$ is hydrogen, loweralkyl, alkanoyl, alkylsulfonyl,

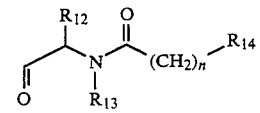

wherein $R_{12}$ and $R_{13}$ are independently hydrogen or loweralkyl, n is 0–2 and $R_{14}$ is substituted or unsubstituted phenyl or heterocyclic; or $XR_7$ together are loweralkylsulfonyl, $N_3$ or Cl, and pharmaceutically acceptable salts thereof.

The chiral centers of the compounds of the invention may have either the "R" or "S" configuration but preferably have an "S" configuration except where noted.

The term "N protecting group" as used herein refers to those groups intended to protect the N-terminus against undesirable reactions during synthetic procedures or to prevent the attack of exopeptidases on the final compounds or to increase the solubility of the final compounds and includes but is not limited to acyl, acetyl, pivaloyl, t-butylacetyl, t-butyloxycarbonyl(Boc), carbobenzyloxycarbonyl or benzoyl groups or an L or D aminoacyl residue, which may itself be N-protected similarly.

The term "loweralkyl" as used herein refers to straight or branched chain alkyl radicals containing from 1 to 6 carbon atoms including but not limited to methyl, ethyl, n-propyl, iso-propyl, n-butyl, iso butyl, sec butyl, n-pentyl, 1-methylbutyl, 2,2-dimethylbutyl, 2-methylpentyl, 2,2-dimethylpropyl, n-hexyl and the like.

The term "arylalkyl" as used herein refers to an unsubstituted or substituted aromatic ring appended to an alkyl radical including but not limited to benzyl, 1 and 2-naphthylmethyl, halobenzyl and alkoxybenzyl.

The term "cycloalkylalkyl" as used herein refers to an alicyclic residue appended to an alkyl radical and includes but is not limited to cyclohexylmethyl and cyclopentylmethyl.

The term "aminoalkyl" as used herein refers to —$NH_2$ appended to a loweralkyl radical.

The term "cyanoalkyl" as used herein refers to —CN appended to a loweralkyl radical.

The term "hydroxyalkyl" as used herein refers to —OH appended to a loweralkyl radical.

The term "alkylamino" as used herein refers to a loweralkyl radical appended to an NH radical.

The term "cycloalkyl" as used herein refers to an aliphatic ring having 4 to 7 carbon atoms.

The term "cycloalkylmethyl" as used herein refers to an cycloalkyl group appended to a methyl radical, including but not limited to cyclohexylmethyl.

The term "aryl" as used herein refers to a substituted or unsubstituted aromatic ring including but not limited to phenyl, naphthyl, halophenyl and alkoxyphenyl.

The terms "alkoxy" and "thioalkoxy" as used herein refer to $R_{15}O$— and $R_{15}S$—, respectively, wherein $R_{15}$ is a loweralkyl group.

The term "alkenyloxy" as used herein refers to $R_{16}O$ wherein $R_{16}$ is an unsaturated alkyl group.

The term "hydroxyalkoxy" as used herein refers to —OH appended to an alkoxy radical.

The term "dihydroxyalkoxy" as used herein refers to an alkoxy radical which is disubstituted with —OH radicals.

The term "arylalkoxy" as used herein refers to an aryl appended to an alkoxy radical.

The term "arylalkoxyalkyl" as used herein refers to an aryalkoxy appended to a loweralkyl radical.

The term "dialkylamino" as used herein refers to —$NR_{17}R_{18}$ wherein $R_{17}$ and $R_{18}$ are independently selected from loweralkyl groups.

The term "(hydroxyalkyl)(alkyl)amino" as used herein refers to —$NR_{19}R_{20}$ wherein $R_{19}$ is hydroxyalkyl and $R_{20}$ is loweralkyl.

The term "N protected aminoalkyl" as used herein refers to $NHR_{21}$ is appended to a loweralkyl group, wherein $R_{21}$ is an N-protecting group.

The term "alkylaminoalkyl" as used herein refers to $NHR_{22}$ appended to a loweralkyl radical, wherein $R_{22}$ is a loweralkyl group.

The term "(N protected)(alkyl)aminoalkyl" as used herein refers to $NR_{21}R_{22}$, which is appended to a loweralkyl radical, wherein $R_{21}$ and $R_{22}$ are as defined above.

The term "dialkylaminoalkyl" as used herein refers to $NR_{23}R_{24}$ appended to a loweralkyl radical wherein $R_{23}$ and $R_{24}$ are independently selected from loweralkyl.

The term "(heterocyclic)alkyl" as used herein refers to a heterocyclic group appended to a loweralkyl radical, including but not limited to imidazolylalkyl.

The term "O-protecting group" as used herein refers to a substituent which protects hydroxyl groups and includes but is not limited to substituted methyl ethers, for example, methoxymethyl, benzyloxymethyl, 2-methoxyethoxymethyl, 2-(trimethylsilyl)ethoxymethyl and tehahydropyranyl; substituted ethyl ethers, for example, 2,2,2-trichloroethyl, t-butyl, benzyl and triphenylmethyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates.

The term "heterocyclic ring" or "heterocyclic" as used herein refers to any 5-, 6-, 9- or 10-membered ring containing from one to three heteroatoms selected from the group consisting of nitrogen, oxygen, and sulfur; having various degrees of unsaturation; wherein the nitrogen and sulfur heteroatoms may optionally be oxidized; wherein the nitrogen heteroatom may optionally be quaternized; and including any bicyclic group in which any of the above heterocyclic rings is fused to a benzene ring. Heterocyclics in which nitrogen is the heteroatom are preferred. Fully saturated heterocyclics are also preferred. Preferred heterocyclics are: pyrryl, pyrrolinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

Saturated heterocyclics may be unsubstituted or monosubstituted with hydroxy, oxo, amino, alkylamino, dialkylamino or loweralkyl. Unsaturated heterocyclics may be unsubstituted or monosubstituted with hydroxy, amino, alkylamino, dialkylamino or loweralkyl.

The most preferred heterocyclics are as follows:

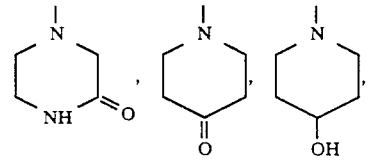

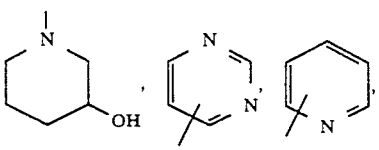

-continued

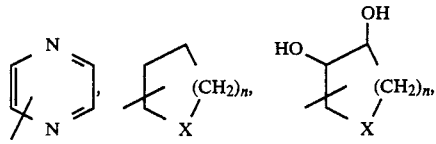

wherein n is 1 or 2 and X is N, NH, O, S, provided that X is the point of connection only when X is N,

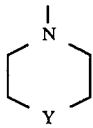

wherein Y is NH, N-loweralkyl, O, S, or SO$_2$, or

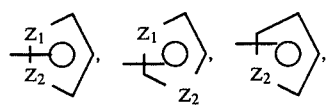

wherein Z$_1$ is N, O, or S and not the point of connection and Z$_2$ is N when it is the point of connection and NH, O or S when it is not the point of connection.

The terms "Ala", "His", "Leu", "Phe" and "Tyr" as used herein refer to alamine, histidine, leucine, phenylalanine and tyrosine, respectively.

The following Examples will serve to further illustrate preparation of the novel compounds of the invention.

EXAMPLE 1

4(S)-t-Butyloxycarbonylamino-5-cyclohexyl-3(R,S)-hydroxy-1-pentene

To a stirred −78° C. solution of Boc-cyclohexylalanine methyl ester (10.2 35.8 mmol) in dry toluene (60 ml) was added diisobutylaluminum hydride (34 ml of a 1.5M solution in toluene). After 30 min., vinyl magnesium bromide (108 ml of 1M solution in tetrahydrofuran (THF)) was added. After stirring for 15 hours at 0° C., the mixture was carefully quenched with methanol, treated with Rochelle salts (22 ml of saturated aqueous solution in 140 ml H$_2$O), and filtered. After extracting the solids 5 times with ethyl acetate, the extracts and filtrate were combined and the organic phase was washed with brine, dried, filtered and evaporated to an oil (10.2 g). Chromatography on silica gel eluting with hexane/ethyl acetate mixtures provided 6.1 g (60%) of the desired product.

Anal. calcd. for C$_{16}$H$_{29}$NO$_3$ ¼H$_2$O: C, 66.8; H, 10.3; N, 4.9. Found: C,66.9; H, 10.2; N, 4.7.

EXAMPLE 2

4(S)-Cyclohexylmethyl-5(R,S)-vinyl-2-oxazolidinone

The resultant product of Example 1 (2.80 g, 9.88 mmol) in dry dimethylformamide (DMF) (50 ml) was added to a stirred suspension of NaH (593 mg of a 60% dispersion in oil, 14.8 mmol, hexane washed) in dry DMF (50 ml). After 3 hours, the mixture was quenched (750 ml water+100 ml brine) and extracted with ether (5×100 ml). The combined organic phase was washed with brine (3×50 ml), dried (MgSO$_4$), filtered and evaporated to an oil (2.23 g). The NMR spectrum of the crude product revealed an 82:18 mixture of 5 S:5 R diastereomers. Silica gel chromatography gave 80% recovery of pure diastereomers. 5 S:

Anal. calcd. for C$_{12}$H$_{19}$NO$_2$: C, 68.9; H, 9.1; N, 6.7. Found: C, 68.4; H, 9.2; N, 6.5. Mass spectrum: (M+1)$^+$=210. 5 R: Mass spectrum: (M+1)$^+$=210.

EXAMPLE 3

(3S,4S)-3-Hydroxy-4-amino-5-cyclohexyl-1-pentene

To the resultant 5S-diasteriomer from Example 2 (2.06 g, 9.84 mmol) in dioxane (180 mL) and water (120 mL) was added barium hydroxide octahydrate (6.24 g, 19.8 mmol). The mixture was refluxed for 18 hours, cooled, filtered, concentrated, taken up in water and extracted with ethyl acetate which was dried over Na$_2$SO$_4$ and evaporated to afford 1.64 g (91%) of the desired product, m.p. 59°–61° C.

Anal. calcd. for C$_{11}$H$_{21}$NO: C, 72.08; H, 11.55; N, 7.64. Found: C, 71.67; H, 11.68; N, 7.36.

EXAMPLE 4

(3S,4S)-3-Hydroxy-4-tert-butoxycarbonylamino-5-cyclohexyl-1-pentene

To the resultant compound from Example 3 (1.62 g, 8.84 mmol) in methylene chloride (20 mL) was added di-tert-butyldicarbonate (1.93 g, 8.84 mmol). The mixture was stirred for 14 hours, diluted with ethyl acetate, washed sequentially with 0.5M H$_3$PO$_4$, saturated NaHCO$_3$ solution and brine, then dried over Na$_2$SO$_4$ and evaporated to afford 2.51 g (100%) of the desired compound.

EXAMPLE 5

(3S,4S)-3-tert-Butyldimethylsilyloxy-4-tert-butoxycarbonylamino-5-cyclohexyl-1-pentene To the resultant compound from Example 4 (0.264 g, 0.932 mmol) in DMF (4 mL) was added tert-butyldimethylsilyl chloride (0.300 g, 1.99 mmol) and imidazole (0.269 g, 3.95 mmol). The mixture was stirred at room temperature for 12 hours, poured into ethyl acetate and washed sequentially with 0.5M H$_3$PO$_4$, saturated NaHCO$_3$ solution and brine, then dried over Na$_2$SO$_4$ and evaporated to afford 0.355 g (96%) of the desired compound. Mass spectrum: (M+H)$^+$=398.

EXAMPLE 6

(2RS,3R,4S)-3-tert-Butyldimethylsilyloxy-4-tert-butoxycarbonylamino-5-cyclohexyl-1,2-oxopentane The resultant compound from Example 5 (0.355 g, 0.893 mmol) in methylene chloride (8 mL) was treated with m-chloroperbenzoic acid (0.758 3.51 mmol) and stirred at ambient temperature for 14 hours. The mixture was concentrated, dissolved in ethyl acetate, washed sequentially with cold 10% aqueous Na$_2$SO$_3$ solution, saturated NaHCO$_3$ solution and brine, and then dried over Na$_2$SO$_4$ and evaporated to afford 0.374 g (100%) of the desired compound. Mass spectrum: (M+H)$^+$=414.

EXAMPLE 7

(2RS,3R,4S)-3-Hydroxy-4-tert-butoxycarbonylamino-5-cyclohexyl-1,2-oxopentane

The resultant compound from Example 6 (2.10 g, 5.07 mmol) was treated with 1M tetrabutylammonium fluoride in tetrahydrofuran (10 mL). The mixture was stirred at 0° C. for 1 hour, poured into ethyl acetate, washed with water and brine, then dried over $Na_2SO_4$ and evaporated. Chromatography on silica gel (0.5% methanol in chloroform) afforded 1.13 g (74%) of the desired compound. Mass spectrum: $(M+H)^+ = 300$.

EXAMPLE 8

(2S,3R,4S)-1-Azido-2,3-dihydroxy-4-tert-butoxycarbonylamino-5-cyclohexylpentane

The resultant compound from Example 7 (1.12 g, 3.74 mmol), ammonium chloride (0.374 g, 6.98 mmol) and sodium azide (0.580 g, 8.92 mmol) were refluxed in methanol (25 mL) for 12 hours. The mixture was concentrated, then taken up in ethyl acetate, washed with water and brine, dried over $Na_2SO_4$ and evaporated. Chromatography on silica gel (20% ether in hexane) afforded 0.461 g (36%) of the desired compound followed by 0.323 g (25%) of the 2-R isomer. M.p. (2S-Diasteriomer): 93°–94° C. Mass spectrum (2S-Diasteriomer): $(M+H)^+ = 343$.

EXAMPLE 9

(2S,3R,4S)-1-Amino-2,3-dihydroxy 4-tert-butoxycarbonylamino-5-cyclohexylpentane

The resultant compound from Example 8 (107 mg, 0.313 mmol) and 10% palladium on carbon (110 mg) in methanol (10 mL) were stirred under a hydrogen atmosphere for 18 hours. The mixture was filtered and evaporated to afford 94.6 mg (96%) of the desired compound, Mass spectrum: $(M+H)^+ = 317$.

EXAMPLE 10

(2S,3R,4S)-1-(3-Methylbutylcarbonylamino)-2,3-dihydroxy 4-tert-butyloxycarbonylamino-5-cyclohexylpentane To the resultant compound from Example 9 (94.6 mg, 0.299 mmol) in methylene chloride (5 mL) at 0° C. was added 4-methylpentanoyl chloride (52ul, 0.37 mmol) and triethylamine (71 μl, 0.51 mmol). The mixture was stirred at 0° C. for 90 min, diluted with ethyl acetate, washed sequentially with 0.5M $H_3PO_4$ solution, 2M NaOH solution and brine, and then dried over $Na_2SO_4$ and evaporated to afford 0.118 g (95%) of the desired compound, m.p. 179°–183° C.

Exact mass calcd. for $C_{22}H_{43}N_2O_5$: 415.3172. Found: 415.3166.

EXAMPLE 11

(2S,3R,4S)-1-(Isobutylsulfonylamino)-2,3-dihydroxy-4-tert butoxycarbonylamino-5-cyclohexylpentane Using the procedure of Example 10 and isobutylsulfonyl chloride rather than 4-methylpentanoyl chloride gave the desired compound. Mass spectrum: $(M+H)^+ = 437$.

EXAMPLE 12

Boc-Phe-d,l-3 -pyrazolylalanine Methyl Ester

To dl 3-pyrazolylalanine methyl ester dihydrochloride (2.05 8.5 mmol) in DMF (10 mL) at −10° C. was added Boc-Phe N-hydroxysuccinimide ester (2.50 g, 6.90 mmol) and N-methylmorpholine (2.8 mL, 25 mmol). The mixture was stirred at −10° C. for 1 hour and then at 25° C. for 12 hours. The mixture was partitioned between ethyl acetate and saturated $NaHCO_3$ solution, and extracted with ethyl acetate which was washed with water, dried over $Na_2SO_4$ and evaporated to afford 2.75 g (95%) of the desired product.

Anal. calcd. for $C_{21}H_{28}N_4O_5$ 0.25 $H_2O$ C, 59.92; H, 6.82; N, 13.31. Found: C, 59.82; H, 6.75; N, 13.13.

EXAMPLE 13

Boc-Phe-d,l-3-pyrazolylalanine

Boc-Phe-DL-3-pyrazolylalanine methyl ester (0.210 g, 0.505 mmol) in dioxane (1.5 mL) and water (1.0 mL) was treated with lithium hydroxide monohydrate (0.0272 g, 0.648 mmol), stirred at 25° C. for 30 minutes and quenched with 0.32 mL 2M HCl. The mixture was poured into chloroform, washed with water, dried over $Na_2SO_4$ and evaporated to afford 0.184 (91%) of the desired compound.

Anal. calcd. for $C_{20}H_{26}N_4O_5 \cdot 0.25H_2O$: C, 59.03; H, 6.56; N, 13.77. Found: C, 58.66; H, 6.70; N, 13.65.

EXAMPLE 14

Boc-Phe-His Amide of (2S,3R,4S)-1-(3-Methylbutylcarbonylamino)-2,3-dihydroxy-4 amino-5-cyclohexylpentane The resultant compound from Example 10 (57.0 mg, 0.138 mmol) was stirred in 4 M HCl/dioxane (1.5 mL) for 1 hour and evaporated. The residue was dissolved in dimethylformamide (0.9 mL) and treated with N methyl-morpholine (33 ul, 0.30 mmol).

To Boc-Phe-His-OH (59.1 mg, 0.147 mmol) and 1 hydroxybenzotriazole (58.0 mg, 0.429 mmol) in dimethylformamide (0.8 mL) at −23° C. was added 1 (3 -dimethylaminopropyl) 3-ethylcarbodiimide hydrochloride (EDAC, 28.7 mg, 0.150 mmol). After stirring at −23° C. for 1 hour, the amine solution was added and the reaction was stirred at −23° C. for 2 hours then at room temperature for 12 hours. The mixture was poured into saturated $NaHCO_3$ solution and extracted with ethyl acetate which was washed with water and brine, then dried over $Na_2SO_4$ and evaporated. Chromatography of the residue on silica gel (3% methanol in chloroform) afforded 21.5 mg (22%) of the desired compound, m.p. 194°–196° C.

EXAMPLE 15

Boc Phe-d,l-3-pyrazolylalanine Amide of (2S,3R,4S)-1-(3 Methylbutylcarbonylamino)-2,3-dihydroxy-4-amino-5-cyclohexylpenrane Using the procedure of Example 14 and Boc-Phe-d,l-3-pyrazolylalanine-OH rather than Boc-Phe-His-OH afforded the desired compound.

Anal. calcd. for $C_{37}H_{58}N_6O_7$ 0.5$H_2O$: C, 62.78; H, 8.40; N, 11.87. Found: C, 62.51; H, 8.17; N, 11.52.

EXAMPLE 16

Boc Phe-His Amide of (2S,3R,4S) 1-(Isobutylsulfonylamino)-2,3-dihydroxy-4-amino-5-cyclohexylpentane Using the procedure of Example 14 with the resultant compound from Example 11 afforded the desired compound, m.p. 94°–97° C. Mass spectrum: $(M+H)^+ = 721$.

EXAMPLE 17

Boc-Phe-His-Amide of (2S,3R,4S)-1-Azido-2,3-dihydroxy-4 amino-5-cyclohexlpentane Using the procedure of Example 14 with the resultant compound from Example 8 afforded the desired compound, m.p. 158°–163° C. Mass spectrum: $(M+H)^+ = 627$.

EXAMPLE 18

Boc-His Amide of (2S,3R,4S)-1-Azido-2,3-dihydroxy 4-amino-5-cyclohexylpentane

Using the procedure of Example 14 with the resultant compound from Example 8 and using Boc-His-OH rather than Boc-Phe-His-OH afforded the desired compound. Mass spectrum: $(M+H)^+ = 480$.

EXAMPLE 19

Boc-(O-methyl)Tyr-His Amide of (2S,3R,4S)-1-Azido-2,3-dihydroxy-4-amino-5-cyclohexylpentane Using the procedure of Example 14 with the product compound of Example 18 and using Boc-(O-methyl)-Tyr-OH rather than Boc-Phe-His-OH afforded the desired compound, m.p. 171°–173° C. Mass spectrum: $(M+H)^+ = 657$.

EXAMPLE 20

Boc-Phe Ala-OH Amide of (2S,3R,4S)-1-Azido-2,3-dihydroxy-4-amino-5-cyclohexylpentane The resultant compound from Example 8 (53.0 mg, 0.155 mmol) was stirred in 4 M HCl/dioxane for 1 hour and evaporated. The residue was taken up in tetrahydrofuran (3 mL), treated with N-methylmorpholine (18 μl, 0.16 mmol) and cooled to 0° C.

To Boc-Phe Ala-OH (58.0 mg, 0.172 mmol) in tetrahydrofuran (2 mL) at 12° C. was added N-methylmorpholine (19 ul, 0.17 mmol) followed by isobutylchloroformate (22 ul, 0.17 mmol). After 3 minutes the amine solution was added and the mixture was stirred for 15 minutes at −12° C. and 2 hours at room temperature. The mixture was diluted with ethyl acetate and washed sequentially with 0.5 M $H_3PO_4$, saturated $NaHCO_3$ solution and brine, then dried over $Na_2SO_4$ and evaporated. Chromatography of the residue on silica gel (3% methanol in chloroform) afforded 86.8 mg (100%) of the desired compound. Mass spectrum: $(M+H)^+ = 561$.

EXAMPLE 21

4(S)-Cyclohexylmethyl-5(R) [1(R,S), 2-oxoethyl]-2-oxazolidinone

To a stirred solution of the 5(R) diastereomer of Example 2 (0.40 g, 1.9 mmol) in dichloromethane (13 ml) was added 3-chloroperoxybenzoic acid (500M %). After 5 days, the mixture was diluted with ether and washed with 1 M $Na_2SO_3$, saturated $K_2CO_3$ and brine. Drying and evaporation provided the desired product (0.34 g, 80%). Mass spectrum: $M^+ = 225$.

EXAMPLE 22

4(S)-Cyclohexylmethyl-5(R)-[1(R,S)-hydroxy-2-(isopropylmercapto)ethyl]-2-oxazolidinone To a stirred solution of the resultant product of Example 21 (0.31 g, 1.38 mmol) in methanol were added triethylamine (0.19 ml) and isopropyl mercaptan (105 mg). The mixture was heated at 50°–60° C. overnight, evaporated and chromatographed on silica gel eluting with ethyl acetate/hexane mixtures to give the 1(R) mer (110 mg, 27%), the 1(S) isomer (70 mg, 17%) and mixed fractions (110 mg, 27%)

Mass spectrum of 1(R) isomer: $M^+ = 301$.
Mass spectrum of 1(S) isomer: $M^+ = 301$.

EXAMPLE 23

4-(S)-Amino-5-cyclohexylmethyl-2(R,S),3(R)-dihydroxy -1 -isopropylmercaptopentane The 1(R,S) mixture of Example 22 (100 mg, 0.33 mmol) and $Ba(OH)_2$ $8H_2O$ (209 mg, 0.66 mmol) were refluxed in 1/1, dioxane/water (8 ml, degassed) for 7 hours. The mixture was then diluted with dioxane, filtered, evaporated, dissolved in dichloromethane, filtered and evaporated. Silica gel chromatography provided 86 mg (96%) of the desired product.

EXAMPLE 24

Boc Phe-His Amide of 4(S)-amino 5-cyclohexylmethyl-2(R),3(R)-dihydroxy-1-isopropylmercaptopentane and Boc Phe-His Amide of 4(S)-amino-5-cyclohexylmethyl-2(S),3(R)-dihydroxy-1-isopropylmercaptopentane The Boc-Phe-His coupling procedure of Example 14 was used, except the amine hydrochloride and N-methylmorpholine were replaced with the resultant product of Example 23, and EDAC was replaced with 1,3-dicyclohexylcarbodiimide (DDC). Separation was achieved on silica gel (9/1, $CH_2Cl_2/CH_3OH$) to give 20% yield of the desired compounds.

Analysis calculated for 2(R) isomer $(C_{34}H_{53}N_5O_6S$ $\frac{3}{4}H_2O)$ C, 60.7; H, 8.2; N, 10.4. Found: C, 60.8; H, 8.2; N, 9.8. FAB mass spectrum: $(M+1)^+ = 660$.

Analysis calculated for 2(S) isomer $(C_{34}H_{53}N_5O_6S$ $\frac{1}{4}H_2O)$ C, 61.0; H, 8.1; N, 10.4. Found: C, 60.9; H, 8.3; N, 10.0 FAB mass spectrum: $(M+1)^+ = 660$.

EXAMPLE 25

Boc-Phe-His Amide of 4(S)-amino-5-cyclohexylmethyl-2-(R),3(R)-dihydroxy-1-(isopropylsulfonyl)pentane A solution of the 2(R) isomer from Example 24 (10 mg, 0.015 mmol) in dichloromethane was treated with chloroperoxybenzoic acid (5.2 mg, 200M %) for 3 hours. The desired compound was isolated in 92% yield after silica gel chromatography (9/1, dichloromethane/methanol). FAB mass spectrum: $(M+1)^+ = 692$.

EXAMPLE 26

4(S)-Cyclohexylmethyl 5(R)-[1(R,S)-hydroxy-2-(isopropyloxy)ethyl]-2-oxazolidinone A solution of the resultant product of Example 21 (0.22 g, 1.0 mmol) in dimethylformamide (DMF, 1.0 mL) was added to a stirred solution of sodium isopropoxide (2.0 mmol) in DMF (9.0 mL). After warming for 24 hours, the mixture was evaporated and then partitioned between 1$\underline{M}$ HCl and ethyl acetate. The organic phase was washed aq. NaHCO$_3$ and brine. Drying and evaporating gave the desired alcohols in 62% yield.

EXAMPLE 27

Boc-Phe-His Amide of 4(S)-Amino-5-cyclohexylmethyl-2-(R),3(R)-dihydroxy 1-isopropyloxypentane and Boc-Phe-His Amide of 4(S)-Amino-5-cyclohexylmethyl-2(S),3(R)-dihydroxy-1-isopropyloxypentane The 1(R,S) mixture of Example 26 was hydrolyzed according to the procedure of Example 23 to give the desired amines which were coupled to Boc Phe-His to the procedure of Example 24. Separation was achieved on silica gel (9/1, CH$_2$Cl$_2$/CH$_3$OH) to give 22% yield of the desired compounds.

EXAMPLE 28

Ethoxycarbonyl-Leu Leu Amide of 4(S)-Amino-5-cyclohexyl 3(R,S)-hydroxy-1-pentene The resultant product of Example 1 (1.05 g, 3.70 mmol) was dissolved in anhydrous 2.2 $\underline{M}$ HCl/CH$_3$OH (70 ml). Evaporation after 16 hours gave the corresponding amine hydrochloride.

To a stirred $-13°$ C. solution of ethoxycarbonyl Leu-Leu-OH (1.17 g, 3.70 mmol) in anhydrous tetrahydrofuran (37 mL) were added N-methylmorpholine (NMM, 0.41 mL) and isobutyl chloroformate (0.50 g). After 3 minutes, a $-13°$ C. THF solution of NMM (0.41 mL) and the above amine hydrochloride were added. The mixture was warmed to room temperature for 6 hours and then partitioned between ethyl acetate (60 mL) and 1 $\underline{M}$ H$_3$PO$_4$ (15 mL). The organic phase was washed with water, aq. NaHCO$_3$ and brine. Drying and evaporating provided 1.76 g (99%) of the desired product. Mass spectrum: M$^+$=481.

Anal. calcd. for C$_{26}$H$_{47}$N$_3$O$_5$: C, 64.8; H, 9.8; N, 8.7. Found: C, 64.6; H, 10.1; N, 8.5

EXAMPLE 29

Ethoxycarbonyl-Leu-Leu Amide of 4(S)-amino-5-cyclohexyl-3(R,S)-hydroxy-1,2(R,S)-oxopentane To a stirred solution of the product of Example 28 (350 mg, 0.727 mmol) in dichloromethane (12 mL) was added 3-chloroperoxybenzoic acid. After 48 hours, the solution was partitioned between ether (28 mL) and 1 $\underline{M}$ Na$_2$SO$_3$ (3 mL). The layers were separated, and the organic phase was washed with 1 $\underline{M}$ Na$_2$SO$_3$, water, saturated NaHCO$_3$ and brine. Drying (Na$_2$SO$_4$) and evaporating provided 0.341 g of the hydroxy epoxide mixture which was used without further purification.

EXAMPLE 30

Ethoxycarbonyl-Leu-Leu Amide of 4(S)-Amino-1-chloro-5-cyclohexyl-2(R,S),3(R,S)-dihydroxypentane To 200 mg (0.402 mmol) of the resultant product of Example 29 was added 4M HCl in anhydrous dioxane (5 ml). After 1 hour, the homogeneous solution was evaporated in vacuo. Chromatography provided the diols in a combined 60% yield.

EXAMPLE 31

Boc-Phe-Ala Amide (4-amino) of (2S,3R,4S)-1,4-Diamino-2,3-dihydroxy-5-cyclohexylpentane A solution of the resultant compound of Example 20 (59.3 mg, 0.106 mmol) in methanol (4 ml) was hydrogenated at atmospheric pressure (10% Pd/C) for 16 hours. Filtration and evaporation provided 49 mg (87%) of the desired compound Mass spectrum: (M+H)$^+$=535.

EXAMPLE 32

Ethoxycarbonyl-Leu-Leu Amide of (2RS,3RS,4S)-Amino-5-cyclohexyl-1,2,3-trihydroxypentane To a stirred solution of the resultant compound of Example 28 (200 mg. 0.415 mmol), N-methylmorpholine N-oxide (112 mg), and OsO$_4$ (0.13 ml of a 2.5 w/v % solution in t-butanol) in THF (10 ml) was added water (1 ml). After 16 hours, brine was added, and the mixture was extracted exhaustively with ether. The combined organic phase was washed sequentially with 10% aqueous Na$_2$SO$_3$, 1M H$_3$PO$_4$, and brine. The solution was dried (Na$_2$SO$_4$), filtered, and evaporated to give 205 mg (96%) of the desired product as a glassy solid. Mass spectrum (M+H)$^+$=516.

EXAMPLE 33

2(S) t-Butyloxycarbonylamino-1-cyclohexyl-3(R,S)-hydroxy-6-methyl-4-heptyne

To a $-78°$ C. solution of n-butyl lithium (51.2 ml of a 0.91M solution in hexane) was added 3-methylbutyne (3.52 g, 51.8 mmol) over the course of 30 seconds. Anhydrous THF (10 ml) was added, and the cold bath was removed for 30 minutes. After cooling the reaction mixture back to $-78°$ C., Boc-cyclohexylalaninal [prepared by Swern oxidation (Mancuso, A. J.; Huang, S.-L.; and Swern, D. *J. Org. Chem.* 1978, 43, 2480) of 5.3 g, 20.7 mmol of Boc-cyclohexylalaninol] in dry THF (5 ml) was added over 5 minutes. After 1 hour the reaction was quenched by addition of NH$_4$Cl (4.01 g, 75 mmol) in water (30 ml). The resulting mixture was partitioned between ether (50 ml) and water (30 ml). The organic phase was washed with water (15 ml), saturated NaHCO$_3$, and brine. Drying and evaporating provided an oil which was chromatographed on SiO$_2$ (ethyl acetate/hexane, 15/85) to give 4.52 g (68%) of the desired product as a 2:1 mixture of hydroxy diastereomers. Mass spectrum: (M+H)$^+$=324.

Anal. calcd. for C$_{19}$H$_{33}$NO$_3$: C, 70 5; H, 10.3; N, 4.3. Found: C, 70.1; H, 10.6; N, 4.3.

EXAMPLE 34

2(S)-t-Butyloxycarbonylamino-1-cyclohexyl-3(R,S)-hydroxy-6-methyl-3(Z)-heptene

The resultant product of Example 4 (0.510 g, 1.70 mmol) and quinoline (0.425 ml) in ethyl acetate (20 ml) were hydrogenated over 10% Pd/BaSO$_4$ (31.8 mg) for 5 hours. The mixture was filtered, the catalyst was washed with ethyl acetate, and the combined organic phase was washed sequentially with 1M HCl (10 ml, 0° C.), water (10 ml), saturated NaHCO$_3$, and brine (10 ml). Drying (Na$_2$SO$_4$) and evaporating in vacuo provided 0.510 g (99%) of the desired product. Mass spectrum: (M+H)$^+$=325.

Anal. calcd. for $C_{19}H_{35}NO_3$: C, 70.1; H, 10.8; N, 4.3. Found: C, 70.3; H, 11.2; N, 4.3.

EXAMPLE 35

2(S)-t-Butyloxycarbonylamino-1-cyclohexyl-6-methyl-3,4,5-trihydroxyheptane

Following the procedure of Example 32, but replacing the resultant product of Example 28 with the resultant compound of Example 34 and increasing the temperature to reflux and the time to 10 days, gave the desired product as a mixture of 4 diastereomers. Chromatography on silica gel provided 3 of them pure eluting in the order shown. Isomer A: mp: 178°–179° C.; Mass spectrum: $M^+ = 359$.

Anal. calcd. for $C_{19}H_{37}NO_5$: C, 63.5; H, 10.4; N, 3.9. Found: C, 63.4; H, 10.1; N, 3.8. Isomer B: mp 148°–149° C.; Mass spectrum: $M^+ = 359$; Found: C, 63.3; 10.2; N, 3.8. Isomer C: mp 151°–152° C.; Mass spectrum: $M^+ = 359$; Found: 63.5; 10.1; N, 3.8.

EXAMPLE 36

Ethoxycarbonyl-Phe-Leu Amide of 2(S)-Amino-1-cyclohexyl-6-methyl-3,4,5-tri-hydroxyheptane; Isomers A, B, and C

Following the procedure of Example 20, but replacing Boc-Phe-Ala with ethoxycarbonyl Phe-Leu and systematically replacing the resultant compound of Example 8 with isomers A, B, and C from Example 35, gave the desired products.

Isomer A: Mass spectrum: $(M+H)^+ = 592$. Anal. calcd. for $C_{32}H_{53}N_3O_7$: C, 65.0; H, 9.0; N, 7.1. Found: C, 65.0; H, 8.9; N, 6.9. Isomer B: Mass spectrum: $(M+H)^+ = 592$. Isomer C: Mass spectrum: $(M+H)^+ = 592$. Found: C, 65 2; H, 9.1; N, 7.0.

EXAMPLE 37

(4S)-2,8-Dimethyl-4-[(toluenesulfonyl)amino]-5-nonanone

To a stirred −78° C. solution of Ts-Leu (15 g, 53 mmol) in dry THF (240 ml) was added n-butyl lithium (57.8 ml of a 0.91M solution in hexane) followed 15 minutes later by isopentyl magnesium bromide (185 ml of a 0.8M solution in THF). The mixture was heated at reflux for 3 days, then cooled and poured into 0° C. 1M HCl (500 ml). The layers were separated and the aqueous phase was extracted with ether (3×150 ml). The combined organic layers were washed with saturated $NaHCO_3$ (2×150 ml) and brine (150 ml). Drying and evaporating provided a residue which was chromatographed on silica gel to give 7.43 (41%) of the desired product. Mass spectrum: $(M+H)^+ = 340$.

Anal calcd. for $C_{18}H_{29}NO_3S$: C, 63.7; H, 8.6, N, 4.1. Found: C, 64.0; H, 8.6; N, 4.1.

EXAMPLE 38

(4S)-2,8-Dimethyl-5-hydroxy-4-[(toluenesulfonyl)amino]-5-vinylnonane

To a stirred 0° C. solution of the resultant compound of Example 37 (79 mg, 0.23 mmol) in dry THF (8 ml) was added vinyl magnesium bromide (1.5 ml of a 1.0M solution in THF) dropwise. The mixture was warmed (room temperature, 10 hours), quenched (8 ml $H_2O+2$ ml brine), acidified with 0.1M $H_3PO_4$ (pH 7), and extracted with ether (3×4 ml). The combined ether phase was washed (4 ml brine), dried ($Na_2SO_4$), filtered, and evaporated to give 81 mg (95%) of the desired product as a 4:1 mixture of diastereomers

EXAMPLE 39

Boc-Phe-Ala Amide of (4S)-Amino-2,8-dimethyl-5-hydroxy-5-vinylnonane, Isomer A

To a solution of the resultant compound of Example 38 (400 mg, 1.09 mmol) in liquid ammonia (80 ml) was added sodium (150 mg, 6.5 mmol). After 6 hours the ammonia was allowed to slowly evaporate under a stream of nitrogen. Benzene (50 ml) and 1:1, ethanol:-water (20 ml) were added with stirring. The layers were separated, and the aqueous phase was extracted with ether. The combined organic phase was dried with $Na_2SO_4$, filtered, and evaporated to give 85 mg (37%) of the desired product.

Following the procedure of Example 20, but replacing the amine hydrochloride and N-methylmorpholine with the above resultant product, gave the desired major diastereomer in 35% yield after chromatography. FAB mass spectrum: $(M+K)^+ = 570$.

Anal. calcd. for $C_{30}H_{49}N_3O_5$: % C, 67.8; H, 9.3; N, 7.9. Found: C, 67.7; H, 9.6; N, 7.3.

EXAMPLE 40

Boc-Phe-Ala Amide of (4S)-Amino-2,8-dimethyl-5-hydroxy-5-vinylnonane, Isomer B

Scale up of the procedure of Example 38 led to the isolation of the minor diastereomer pure after chromatography. Treatment as in Example 39 provided the desired isomer of the resultant product of Example 39.

EXAMPLE 41

Boc-Phe-Ala Amide of 4(S)-Amino-3-isopentyl-6-methyl-1,2,3-trihydroxyheptane, Isomer A

Following the procedure of Example 32, but replacing the resultant compound of Example 28 with the resultant compound of Example 39 gave the desired product.

EXAMPLE 42

Boc-Phe-Ala Amide of 4(S)-Amino-3-isocentyl-6-methyl-1,2,3-trihydroxyheptane, Isomer B

Following the procedure of Example 32, but replacing the resultant compound of Example 28 with the resultant compound of Example 40, gave the desired diastereomer of the resultant product of Example 41.

EXAMPLE 43

Ethoxycarbonyl-Phe-Leu Amide of 2(S)-Amino-1-cyclohexyl-6-methyl-3,4,5-trihydroxyheptane, Isomers D, E, F, and G

Following the $Na/NH_3$ reduction procedure of Example 39, but replacing the resultant compound of Example 38 with the resultant product of Example 33 gave the corresponding 3(E) heptene isomer of the resultant compound of Example 34 which was oxidized according to the procedure of Example 35. In this way the four isomeric 2(S)-t-butyloxycarbonyl-amino-1-cyclohexyl-6-methyl-3,4,5-trihydroxyheptanes were isolated, separated, and converted to the desired products according to the procedure of Example 36.

EXAMPLE 44

Boc-His-Amide of (2S,3R,4S)-1-(3-Methylbutylcarbonylamino)-2,3-dihydroxy-4-amino-5-cyclohexylpentane Following the procedure of Example 18, but replacing the resultant compound of Example 8 with the resultant compound of Example 10, provided the desired compound.

EXAMPLE 45

Dibenzylacetyl His Amide of(2S,3R,4S)-1-Azido-2,3-dihydroxy-4-amino-5-cyclohexylpentane Using the procedure of Example 14 with the resultant compound from Example 18 and dibenzylacetic acid rather than Boc-Phe-His-OH gave the desired compound.

EXAMPLE 46

Isobutyryl (O-methyl)tyrosine

To (O-methyl)tyrosine (126 mg, 0 647 mmol) in dioxane (3 ml) was added NaOH (52 mg, 1.3 mmol) in water (3 ml). Isobutyric anhydride (0.11 ml, 0.66 mmol) was added and the mixture was stirred at 0° C. for 2 h, poured into saturated $NaHCO_3$ solution and extracted with ether.

The aqueous phase was acidified with conc. HCl then extracted with ethyl acetate which was dried over $Na_2SO_4$ and evaporated. Trituration with hot ethyl acetate afforded 132 mg (77%) of the desired product as a solid.

Anal. calcd. for $C_{14}H_{19}NO_4 \cdot 0.25 H_2O$: C, 62.32; H, 7.28; N, 5.19.

Found: C, 62.68; H, 7.29; N, 5 18.

EXAMPLE 47

Isobutyryl-(O-methyl)Tyr-His Amide of (2S,3R,4S)-1-Azido-2,3-dihydroxy-4-amino-5-cyclohexylpentane Using the procedure of Example 14 with the resultant compound from Example 18 and using the resultant compound from Example 46 instead of Boc-Phe-His-OH afforded the desired compound, m.p. 201°–204° C.

Exact mass calculated for $C_{31}H_{47}N_8O_6$ (M+H): 627.3618 Found: 627.3611.

EXAMPLE 48

Boc-1-Nal-His Amide of (2S,3R,4S)-1-Azido-2,3-dihydroxy-4-amino-5-cyclohexylpentane Using the procedure of Example 14 with the resultant compound from Example 18 and using Boc-napthylalanine (Boc-1-Nal) rather than Boc-Phe-His-OH provided the desired compound.

EXAMPLE 49

Isobutyryl (phenylmethyl)alanine

Prepared from phenylmethylalanine according to the procedure of Example 46 to give the desired product as an oil.

EXAMPLE 50

Isobutyrl(phenylmethyl)alanine-His Amide of (2S,3R,4S)-1-Azido-2,3-dihydroxy-4-amino-5-cyclohexylpentane Using the procedure of Example 14 with the resultant compound from Example 18 and using isobutyryl (phenylmethyl)alanine rather than Boc-Phe-His-OH gave the desired compound.

Exact mass calcd for $C_{31}H_{47}N_8O_5$ (M+H): 611.3669. Found: 611.3649.

EXAMPLE 51

Isobutyryl (O-benzyl)threonine

This compound was prepared according to the procedure of Example 46 from (O-benzyl)threonine, yielding the desired product as a solid.

Anal. calcd. for $C_{15}H_{21}NO_4$: C, 64.50; H, 7.58; N, 5.01.

Found: C, 64.65; H, 7.51; N, 4.75.

EXAMPLE 52

Isobutyryl (O-benzyl)Thr-His Amide of (2S,3R,4S)-1-Azido-2,3-dihydroxy-4-amino-5-cyclohexylpentane Using the procedure of Example 14 with the resultant compound from Example 18 and isobutyryl (O-benzyl)threonine rather than Boc-Phe-His-OH gave the desired compound.

Exact mass calcd. for $C_{32}H_{49}N_8O_6$ (M+H): 641.3775. Found: 641.3777.

EXAMPLE 53

1-Benzyloxycarbonylamino-2,3-propanediol

1-Amino-2,3-propanediol (15.2 g, 167 mmol) and NaOH (8.1 g, 204 mmol) in water (70 ml) at −10° C. was treated dropwise with benzyl chloroformate (28.5 ml, 200 mmol) in ether (30 ml) over 20 min. The reaction was stirred at 0° for 30 min then at room temperature for 2 h. The mixture was acidified with 2M HCl and extracted with ethyl acetate which was washed with 0.5M $H_3PO_4$ and brine, then dried over $Na_2SO_4$ and evaporated. Recrystallization of the residue from benzene afforded 16.59 g (44%) of the desired product as a white powder. NMR (300 MHz, $CD_3OD$, ppm): 3.12 (dd, 1H), 3.28 (dd, 1H), 3.50 (m, 2H), 3.68 (m, 1H), 5.08 (s, H), 7.35 (m, 5H).

EXAMPLE 54

1-Methylamino-2,3-propanediol

Lithium aluminum hydride (7.20 g, 189 mmol) in tetrahdyrofuran (THF, 300 ml) was heated to reflux and the resultant compound from Example 53 (17.0 g, 75.5 mmol) in THF (150 ml) was added dropwise over 10 min. The mixture was refluxed for 2 h, cooled, quenched sequentially with water (10 ml), 3M NaOH (40 ml) and water (20 ml), then filtered and concentrated. The residue was dissolved in water which was washed with ether and evaporated. Bulb to bulb distillation of the residue afforded 2.0 g (25%) of the desired compound as an oil. NMR (300 MHz, $CDCl_3$, ppm): 2.45 (s, 3H), 2.68 (dd, 1H), 2.77 (dd, 1H), 3.61 (dd, 1H), 3.72 (dd, 1H), 3.78 (m, 1H).

EXAMPLE 55

(N-Methyl-2,3-dihydroxypropylamino)carbonyl-(O-methyl)tyrosine Methyl Ester

To the resultant compound from Example 62 (1.53 g, 6.5 mmol) in dioxane (5 ml) at 0° C. was added the resultant compound from Example 54 (0.684 g, 6.5 mmol). The reaction was stirred at 0° C. for 1 h then at room temperature for 1 h, evaporated and chromatographed on silica gel with 5% methanol in chloroform to afford 1.855 g (84%) of the desired product as an oil. NMR (300 MHz, CDCl$_3$, ppm), 2.88, 2.89 (s, 3H total), 3.05 (m, 2H), 3.26–3.60 (m, 5H), 3 73 (s, 3H), 3.80 (s, H), 4.70 (m, 1H), 5.07 (broad t, 1H), 6.83 (dd, 1H), 7.02 (dd, 1H).

EXAMPLE 56

(N-Methyl 2,3-dihydroxypropylamino)carbonyl-(O-methyl)tyrosine

The resultant compound from Example 55 (114 mg, 0.355 mmol) in dioxane (4 ml) and water (2 ml) at 0° C. was treated with LiOH monohydrate (42.0 mg, 1 mmol). After 90 min 2M HCl (0.6 ml, 1.2 mmol) was added and the mixture was evaporated to a foam which was used without further purification, DCI-MS: (M+H)=327.

EXAMPLE 57

Dimethylaminocarbonyl-(O-methyl)tyrosine Methyl Ester

Prepared from dimethyl amine and the resultant compound from Example 62 according to the procedure for Example 55.

EXAMPLE 58

Dimethylaminocarbonyl-(O-methyl)-tyrosine

Prepared according to the procedure of Example 56 from the resultant compound of Example 57 with the modification that the product was isolated by pouring the reaction mixture into 2M HCl and extracting with ethyl acetate which was dried over Na$_2$SO$_4$ and evaporated. EI-MS: M+ = 266.

Anal. calcd. for C$_{13}$H$_{18}$N$_2$O$_4$: C, 58 64; H, 6.81; N, 10 52.

Found: C, 58.44; H, 6.87; N, 9.95.

EXAMPLE 59

3,3-Dimethylglutaric Acid Mono t-Butyl Ester 3,3-Dimethylglutaric anhydride (455 mg, 3.2 mmol) in tetrahydrofuran (THF, 5 mL) was treated with sublimed potassium t-butoxide (395 mg, 3.5 mmol). After 30 min the solution was concentrated, poured into saturated NaHCO$_3$ solution and washed with ether. The aqueous phase was acidified to pH 4 with 0.5M H$_3$PO$_4$ and extracted with chloroform which was dried over Na$_2$SO$_4$ and evaporated to afford 179 mg (26%) of the desired product as an oil. NMR (300 MHz, CDCl$_3$, ppm), 1.13 (s, 6H), 1.47 (s, 9H), 2.33 (s, 2H), 2.45 (s, 2H).

EXAMPLE 60

(4-t-Butyloxycarbonyl-3,3-dimethyl)butanoyl-phenylalanine Benzyl Ester

Prepared according to the procedure from Example 20 from the resultant compound from Example 59 and phenylalanine benzyl ester p-toluenesulfonic acid salt. NMR (300 MHz, CDCl$_3$, ppm), 0 96 (s, 3H), 1.00 (s, 3H), 1 44 (s, 9H), 1.90 (d, 1H), 2.16 (d, 1H), 2.25 (d, 1H), 2.29 (d, 1H), 3.03 (dd, 1H), 3.17 (dd, 1H), 4.92 (m, 1H), 5.12 (d, 1H), 5.16 (d, 1H), 7.10–7.40 (m, 10H).

EXAMPLE 61

(4-t-Butyloxycarbonyl-3,3-dimethyl)butanoyl-phenylalanine

The resultant compound from Example 60 and an equal weight of 10% Pd on carbon in methanol were stirred under a hydrogen atmosphere for 3 h. The reaction was filtered and evaporated to provide to desired product as an oil. NMR (300 MHz, CDCl$_3$, ppm), 0.93 (s, 3H), 0.99 (s, 3H), 1.45 (s, 9H), 1.77 (d, 1H), 2.10 (d, 1H), 2.19 (d, 1H), 2.25 (d, 1H), 3.02 (dd, 1H), 3.33 (dd, 1H), 4.72 (m, 1H), 7.25 (m, 5H).

EXAMPLE 62

α-Isocyanato-L-(O-methyl)tyrosine

A suspension of (O-methyl)tyrosine methyl ester hydrochloride (6 g) in toluene (125 ml) was heated at 100° C. while phosgene was bubbled into the reaction mixture. After 2 h the mixture became homogeneous and the phosgene was continued for an additional 15 min. The mixture was cooled and evaporated with several benzene chasers to provide the desired product.

EXAMPLE 63

Morpholine-(O-methyl)Tyrosine Methyl Ester

Prepared from morpholine and the resultant compound from Example 62 according to the procedure for Example 55.

EXAMPLE 64

Morpholino-(O-methyl)tyrosine

Using the procedure from Example 58 with the resultant compound from Example 63 gave the desired product.

Anal calcd. for C$_{15}$H$_{20}$N$_2$O$_5$—0.25 H$_2$O: C, 57.59; H, 6.66; N, 8.95.

Found: C, 57.79; H, 6.57; N, 8.93.

EXAMPLE 65

Boc-6-aminohexanoic Acid

A mixture of 3.0 g (0.02 mol) of 6-aminohexanoic acid, 5.04 g (0.02 mol) of di-t-butyldicarbonate and 3.84 g (0.05 mmol) of NaHCO$_3$ in 160 ml of 1:1 H$_2$O/tetrahydrofuran was stirred vigourously for 24 h. After concentration of the solvent, the mixture was acidified with HCl, saturated with NaCl, extracted with ethyl acetate, dried over MgSO$_4$ and concentrated in vacuo to give the desired product (R$_f$0.48, 9:1 chloroform/methanol).

EXAMPLE 66

Boc-6-aminohexanoyl-Phe Benzyl Ester

A solution of 1.50 g (6.5 mmol) of the resultant compound of Example 65, 2.77 g (6.5 mmol) of phenylalanine benzyl ester p-toluenesulfonate salt, 0.87 g (6.5 mmol) of 1-hydroxybenzotriazole hydrate, 1.19 ml (8.4 mmol) of triethylamine and 1.74 g (8.4 mmol) of dicyclohexylcarbodiimide in 150 ml of tetrahydrofuran was allowed to stir at ambient temperature for 18 h. After concentration in vacuo, the residue was taken up in 300 ml of ethyl acetate, filtered, washed consecutively with 1M HCl, H$_2$O, saturated NaHCO$_3$, H$_2$O and saturated NaCl; dried over MgSO$_4$ and concentrated. Purification by flash column chromatogrpahy using 4:1 chloroform-/ethyl acetate gave 2.35 g (77%) of the desired compound (R$_f$ 0.21, 4:1 chloroform/ethyl acetate).

EXAMPLE 67

Boc-6-aminohexanoyl-Phe-OH

A mixture of 0.5 g (1.07 mmol) of the resultant compound of Example 66 and 30 mg of 10% palladium on carbon in 50 ml of methanol was stirred under an H$_2$ atmosphere for 3.5 h. After filtration through Celite, concentration in vacuo gave the desired compound.

EXAMPLE 68

(N-Methyl-2,3-dihydroxypropylamino)carbonyl (O-methyl)Tyr-His Amide of (2S,3R,4S)-1-Azido-2,3-dihydroxy-4-amino-5-cyclohexylpentane Using the procedure of Example 14 with the resultant compound from Example 18 and using the resultant compound from Example 56 instead of Boc-Phe-His-OH gave the desired compound.

EXAMPLE 69

Dimethylaminocarbonyl (O-methyl)Tyr-His Amide of (2S,3R,4S)-1-Azido-2,3-dihydroxy-4-amino-5-cyclohexylpentane Using the procedure of example 14 with the resultant compound from Example 18 and using the resultant compound from Example 58 instead of Boc-Phe-His-OH gave the desired compound. FAB-MS: (M+H)=628.

EXAMPLE 70

(4-t-Butyloxycarbonyl-3,3-dimethyl)butanoyl-Phe-His Amide of (2S,3R,4S)-1-Azido-2,3-dihydroxy-4-amino-5-cyclohexylpentane Using the procedure of Example 14 with the resultant compound from Example 18 and using the resultant compound from Example 61 rather than Boc-Phe-His-OH afforded the desired compound. FAB-MS: (M+H)=725.

EXAMPLE 71

(4-Hydroxycarbonyl-3,3-dimethyl)butanoyl-Phe-His Amide of (2S,3R,4S)-1-Azido-2,3-dihydroxy-4-amino-5-cyclohexylpentane Trifluoroacetic Acid Salt The resultant compound from Example 70 (35 mg) was stirred for 24 h in 2 ml methylene chloride and 1 ml trifluoroacetic acid. Evaporation of the solvent and trituration of the residue with ether afforded 21 mg (56%) of the desired product as a solid.
Exact mass calcd. for C$_{33}$H$_{49}$N$_8$O$_7$ (M+H)=669.3724.
Found: 669.3746.

EXAMPLE 72

Morpholinocarbonyl (O-methyl)Tyr-His Amide of (2S,3R,4S)-1 Azido-2,3-dihydroxy-4-amino-5-cyclohexylpentane Using the procedure of Example 14 with the resultant compound from Example 18 and using morpholinocarbonyl-(O-methyl)tyrosine rather than Boc-Phe-His-OH afforded the desired compound, m.p. 85°–90° C. FAB-MS: M+H=670.

EXAMPLE 73

Boc-6-aminohexanoyl-Phe-His Amide of (2S,3R,4S)-1-Azido-2,3-dihydroxy-4-amino-5-cyclohexylpentane Using the procedure of Example 14 with the resultant compound from Example 18 and using the resultant compound from example 67 rather than Boc-Phe-His-OH gave the desired compound.

EXAMPLE 74

6-Aminohexanoyl-Phe-His Amide of (2S,3R,4S)-1-Azido-2,3-dihydroxy-4-amino-5-cyclohexylpentane di-HCl Salt The resultant compound from Example 73 was stirred for 1 h at 0° C. in 4M HCl/methanol. Evaporation of the solvent gave the desired product.

EXAMPLE 75

3-Benzyloxycarbonylamino-3-methylbutanoic Acid

A solution of 2,2-dimethyl-3-carbomethyloxypropionic acid [LeMaul, Bull. Soc. Chim. Fr., 828 (1965), 20 g, 0.125 mol], diphenylphosphorylazide (34.3 g, 0.125 mol) and triethylamine was heated in toluene (150 ml) at 100° C. for 2 h. After cooling to 5° C., the toluene solution was washed successively with 0.5M HCl, aqueous NaHCO$_3$ and brine. Evaporation of the dried solution gave a residue which was chromatographed on silica gel eluting the 60/40 hexane-ether. There was obtained 13 g of methyl 3-isocyanato-3-methylbutanoate as a mobile liquid. A solution of this material in toluene (20 ml) was treated with benzyl alcohol (13 ml) and the resulting mixture heated at reflux for 40 h. Evaporation of the toluene left a residue which was dissolved in methanol (125 ml) and then treated with a solution of NaOH (6.6 g, 0.165 mol) in 22 ml of water. After 5 h, the reaction mixture was partially evaporated, washed with ether and acidified with 6N HCl. Extraction with methylene chloride and evaporation gave 21 g of the desired product. NMR (300 MHz. CDCl$_3$): 1.42 (s, 6H), 2.78 (s, 2H), 5.08 (s, 2H).

EXAMPLE 76

Cbz-[(β,β-di-Me)-β-Ala]-Phe-OCH$_3$

A 4.0 9 sample of 3-benzyloxycarbonylamino-3-methylbutanoic acid was coupled to phenylalanine methyl ester hydrochloride (3.43 g) using the mixed anhydride procedure described in Example 20. Purification of the crude product by flash chromatography eluting with 65/35 ether-hexane gave an 86% yield of product. NMR (300 MHz, CDCl$_3$): 1.32 (s, 3H), 1.34 (s, 3H), 2.46 (d, 1H), 2.63 (d, 1H), 2.98 (dd, 1H), 3.09 (dd, 1H), 3.70 (s, 3H), 4.86 (dd, 1H), 4.97 (d, 1H), 5.2 (d, 1H), 5.3 (s, 1H), 6.13 (d, 1H).

EXAMPLE 77

Cbz-[(β,β-di-Me)-β-Ala]-Phe-OH

To a 0° C. solution of Cbz-[(β,β-di-Me)-β-Ala]-Phe-OMe (1.5 g, 3.63 mmol) in dioxane (15 ml) was added a solution of lithium hydroxide (0.174 g, 4.15 mmol) in water (7.5 ml). After stirring for 1 h at 0°–5° C., the reaction mixture was diluted with cold water and extracted twice with ether. The aqueous portion was acidified with 6N HCl and extracted with ether. The organic extract was washed with brine and evaporated to give an 87% yield of product as a viscous liquid.

EXAMPLE 78

Cbz-[(β,β-di-Me)-β-Ala]-Phe-His Amide of (2S,3R,4S)-1-(3-methylbutylcarbonylamino)-2,3-dihydroxy-4-amino-5-cyclohexylpentane The resultant compound from Example 44 (0.138 mmol) was stirred in 4M HCl/dioxane (1.5 ml) for 1 h and evaporated. The residue was dissolved in dimethylformamide (0.9 ml) and treated with N-methylmorpholine (33 ul, 0.30 mmol). To Cbz-[(β,β-di-Me)-β-Ala]-Phe-OH (0.147 mmol) and 1-hydroxybenzotriazole (58.0 mg, 0.429 mmol) in dimethylformamide (0.8 ml) at −23° C. was added 1-(3-dimethylaminopropyl)-3-ethylcarbodiimide hydrochloride (EDAC, 28.7 mg, 0.150 mmol) After stirring at −23° C. for 1 h, the amine solution was added and the reaction was stirred at −23° C. for 2 h then at room temperature for 12 h. The mixture was poured into saturated NaHCO$_3$ solution and extracted with ethyl acetate which was washed with water and brine, then dried over Na$_2$SO$_4$ and evaporated. Chromatography of the residue on silica gel (3% methanol in chloroform) afforded (22%) of the desired compound.

EXAMPLE 79

H-[β,β-di-Me)-β-Ala]-Phe-His Amide of (2S,3R,4S)-1-(3-methylbutylcarbonylamino)-2,3-dihydroxy-4-amino-5-cyclohexylpentane The resultant compound of Example 78 (0.12 mmol) in acetic acid (10 ml) was hydrogenated at 1 atmosphere with 10% Pd/C (0.05 g) for 3 h. Filtration, extraction of the catalyst with acetic acid, and evaporation of the combined acetic acid solutions gave a residue which was dissolved in water (25 ml) and lyophilized to provide a 91% yield of the desired product.

EXAMPLE 80

3-Benzyloxycarbonylamino-2,2-dimethylpropionic Acid

3-Carbomethoxy-3-methylbutanoic acid [*Bull. Soc. Chim. Fr.*, 828 (1965), 7.85 g, 0.049 mol] was reacted with diphenylphosphorylazide and triethylamine as described in Example 75. After heating the toluene solution for 1.5 h, benzyl alcohol (8 g) was added directly to the reaction mixture and heating at reflux was continued for 20 h. Work-up and purification as in Example 75 gave methyl 3-benzyloxycarbonylamino-2,2-dimethylpropionate. NMR (300 MHz, CDCl$_3$): 1.2 (s, 6H), 3.3 (d, 2H), 3.68 (s, 3H), 5.1 (s, 2H), 5.22 (m, 1H). A sample of the methyl ester (6.21 g, 0.23 mol) was saponified with 3.1 g (0.78 mol) of NaOH in 100 ml ethanol/10 ml H$_2$O at room temperature for 48 h. Work-up as in Example 75 gave the desired product as a liquid. NMR (300 MHz, CDCl$_3$) 1.23 (s, 6H), 3.32 (d, 2H), 5.10 (s, 2H), 5 27 (m, 1H).

EXAMPLE 81

Cbz-[(α,α-di-Me)-β-Ala]-Phe-OCH$_3$.

To a solution of 3-benzyloxycarbonylamino-2,2-dimethylpropionic acid (1.5 g, 5.97 mmol) in methylene chloride (13 ml) was added oxalyl chloride (0.757 g, 5.97 mmol) and dimethylformamide (30 ul). After stirring for 1 h at room temperature, the reaction mixture was cooled to 0° C. and treated successively with phenylalanine methyl ester HCl (1.29 g, 5.97 mmol) and N-methylmorpholine (1.81 g, 17.9 mmol). Stirring for 1 h at 0°–5° C. was followed by distribution between CH$_2$Cl$_2$ and 0.5N HCl. The organic phase was washed with aqueous NaHCO$_3$ and brine and dried over MgSO$_4$. Evaporation of the solvent gave a residue which was purified by chromatography. There was obtained a 69% yield of product as a liquid. NMR (300 MHz, CDCl$_3$): 1.11 (s, 3H), 1.12 (s, 3H), 3.05 (dd, 1H), 3.18 (dd, 1H), 3.23 (d, 1H), 3.24 (d, 1H), 3.75 (s, 3H), 4.82 (dd, 1H), 5.08 (s, 2H), 5.37 (broad t, 1H), 6.04 (d, 1H).

EXAMPLE 82

Cbz-[(α,α-di-Me)-β-Ala]-Phe-OH.

The hydrolysis of the methyl ester described in Example 81 was carried out by the procedure described in Example 75 to give the desired product in 90% yield as a viscous liquid.

EXAMPLE 83

H-[(α,α-di-Me)-β-Ala]-Phe-His Amide of (2S,3R,4S)-1-(3-methylbutylcarbonylamino)-2,3-dihydroxy-4-amino-5-cyclohexylpentane.

Using the procedures described in Examples 78 and 79, Cbz-[(α,α-di-Me)-β-Ala]- Phe-OH was converted to the desired product.

EXAMPLE 84

2(S)-[[(4 Morpholinyl)carbonyl]oxy]-3-phenylpropionic Acid Methyl Ester.

To L-phenyllactic acid methyl ester (3.2 g) was added 150 ml of 12.5% phosgene in toluene and 25 drops of dimethylformamide. After stirring for 16 h at room temperature, the solvent was evaporated and the residue chased several times with benzene. The resulting product was dissolved in methylene chloride (50 ml), cooled to 0° C. and treated by dropwise addition with 3.86 g (0.044 mol) of morpholine. The reaction mixture was stirred for 2 h at 0°–5° C. and then distributed between 0.5N HCl and methylene chloride. The organic phase was washed with aqueous NaHCO$_3$ and brine and evaporated to a residue. Flash chromatography on silica gel eluting with 2/1 ether-hexane gave a 65% yield of product. NMR (300 MHz): 3.08 (dd, 1H), 3.20 (dd, 1H), 3.8 (s, 3H), 5.19 (dd, 1H).

EXAMPLE 85

2(S)-[(4-Morpholinyl)carbonyl]oxy-3-phenylpropionic Acid

Using the hydrolysis procedure of Example 77, the title compound was obtained in 90% yield.

EXAMPLE 86

2(S)-[(4-Morpholinyl)carbonyl]oxy-3-phenylpropionyl-His Amide of (2S,3R,4S) 1-(3-methylbutylcarbonylamino)-2,3-dihydroxy-4-amino-5-cyclohexylpentane.

Using the procedure of Example 78, but replacing Cbz-[(β,β-di-Me)-β-Ala]-Phe-OH with the product of Example 85 gave the desired final product.

EXAMPLE 87

2(R,S)-(4-Morpholinylcarbonylmethyl)-3-phenylpropionic Acid.

Ethyl α-carboxymethylcinnamate was prepared as reported (Cohen, S. G. and Milovanovic, A. Biochemistry, 1968, 3495) and hydrogenated (1 atmosphere $H_2$) with 10% Pd/C in methanol for 5 h. The resulting dihydro cinnamate was coupled to morpholine using the procedure of Example 20. Ester hydrolysis according to the procedure of Example 77 provided the desired compound. Mass spectrum: $(M+H)^+ = 278$.

Anal calcd. for $C_{15}H_{19}NO_4 \cdot \frac{1}{2}H_2O$: C, 64.4; H, 6.9; N, 5.0.

Found: C, 64.4; H, 6.8; N, 4.9.

EXAMPLE 88

2(R,S)-(4 Morpholinylcarbonylmethyl)-3-phenylpropionyl-His Amide of (2S,3R,4S)-1-(3-methylbutylcarbonylamino)-2,3-dihydroxy-4-amino-5-cyclohexylpentane.

Using the procedure of Example 78, but replacing Cbz-[(β,β-di-Me)-β-Ala]-Phe-OH with 2(R,S)-(4-morpholinylcarbonylmethyl)-3-phenylpropionic acid provided the desired product as a mixture of R and S diastereomers. Chromatography on silica (dichloro methane/methanol 95/5-90/10) provided the less polar diastereomer (isomer A) and the more polar diasrereomer (isomer B).

EXAMPLE 89

2(S)-(Isobutyryloxy)-3-phenylpropionyl-His Amide of (2S,3R,4S) 1-(3-methylbutylcarbonylamino)-2,3-dihydroxy-4-amino-5-cyclohexylpentane.

Using the procedure of Example 78, but replacing Cbz-[(β,β-di-Me)-β-Ala]-Phe-OH with O-isobutyryl-L-3-phenyllactic acid gave the desired product.

EXAMPLE 90

Cbz-Phe-His Amide of (2S,3R,4S)-1-(3methylbutylcarbonylamino)-2,3-dihydroxy-4-amino-5-cyclohexylpentane.

Using the procedure of Example 78, but replacing Cbz-[(β,β-di-Me)-8-Ala]-Phe-OH with Cbz Phe-OH gave the desired product.

EXAMPLE 91

H-Phe-His Amide of (2S,3R,4S)-1(3-methylbutylcarbonylamino)-2,3-dihydroxy-4-amino-5-cyclohexylpentane A solution of the product from Example 90 (0.273 mmol) in methanol (50 ml) was hydrogenolyzed in a Parr Apparatus with 90 mg of 20% Pd/C and 4 atmospheres of hydrogen. After the hydrogen uptake ceased, the catalyst was filtered and the filtrate evaporated to the desired product in 68% yield.

EXAMPLE 92

α-Aminoisobutyryl-Phe His Amide of (2S,3R,4S)-1-(3-methylbutylcarbonylamino) 2,3-dihydroxy-4-amino 5-cyclohexylpentane.

A mixture of α-aminoisobutyric acid N-carboxy anhydride (10.9 mg, 0.085 mmol) and the product from Example 91 (0.085 mmol) in dimethylformamide (3 ml) was stirred at room temperature for 16 h. The dimethylformamide was evaporated in vacuo and the residue was distributed between chloroform and water. The organic phase was dried and evaporated to a residue which was chromatographed on silica gel eluting with methanolform mixtures. There was obtained a 43% yield of

EXAMPLE 93

2(S)-[(2-Benzyloxycarbonylamino-2-methyl)propyl]oxy-3-phenylpropionyl-His Amide of (2S,3R,4S)-1-(3-methylbutylcarbonylamino)-2,3-dihydroxy-4-amino-5-cyclohexylpentane.

2(S)-[(2-Benzyloxycarbonylamino 2-methyl)-propyl]oxy-3 phenylpropionic acid was prepared by the methodology described by E. D. Nicolaides, et al., *J. Med. Chem.*, 29, 959 (1986). This acid was substituted for Cbz-[(β,β-di-Me)-β-Ala]-Phe-OH using the procedure in Example 85 to give the title compound.

EXAMPLE 94

2(S)-[(2-Amino-2-methyl)propyl]oxy-3-phenylpropionyl-His Amide of (2S,3R,4S)-1-(3-methylbutylcarbonylamino)-2,3-dihydroxy-4-amino-5-cyclohexylpentane.

Using the procedure of Example 79, the product of Example 93 was hydrogenolyzed to give the desired product.

EXAMPLE 95

Ethyl hydrogen (α,α-dimethylbenzyl)malonate.

Diethyl (α,α-dimethylbenzyl)malonate was prepared by the congugate addition of phenyl magnesium bromide to diethyl isopropylidenemalonate as described by C. Holmberg [Liebigs Ann Chem , 748 (1981)]. A solution of this diester (42.1 g, 0.15 mole) in ethanol (100 ml) was treated by dropwise addition with a solution of potassium hydroxide (8.48 g, 0.13 mole) in 100 ml of ethanol. After heating at 90° C. for 1 h and at 50° C. for 20 h, the reaction mixture was evaporated on the rotary evaporator to a residue. The residue was diluted with water and extracted with ether to remove unreacted starting material. The aqueous phase was cooled to 5° C., acidified to pH 3 with 6N HCl, and extracted with methylene chloride. The organic layer was washed with brine solution and dried over magnesium sulfate. Evaporation of the solvent gave 27.3 g (84%) of liquid product. NMR (CDCl$_3$): 1.05 (3H, t), 1.6 (6H, s), 3.78 (1H, s), 3.96 (2H, m), 7.2–7.4 (5H, m).

EXAMPLE 96

Ethyl 2(R,S) [[(4-morpholinyl)carbonyl]amino]-3,3-dimethyl-3-phenylpropionate.

To a solution of ethyl hydrogen (α,α-dimethylbenzyl)malonate (4 g, 0.016 mole) in toluene was added triethylamine (2.23 ml, 0.016 mole) and diphenylphosphoryl azide (4.4 g, 0.016 mole). The reaction mixture was heated at 100° C. for 2.5 h, cooled to 5° C., and treated with 1.4 ml (0.016 mole) of morpholine. After stirring overnight at room temperature, the toluene solution was washed successively with 1N HCl and aqueous sodium bicarbonate solution. The dried organic solution was evaporated to a residue which was purified by column chromatography on silica gel. There was obtained 3.7 g (69%) of product after trituration with hexane, m.p. 93°–94° C.

Anal. calcd. for $C_{18}H_{26}N_2O_4$: C, 64.65; H, 7.84; N, 8.38.

Found: C, 64.72; H, 7.95; N, 8.33.

EXAMPLE 97

2(R,S)-[[(4-Morpholinyl)carbonyl]amino]-3,3-dimethyl-3-phenylpropionic acid.

A solution of the product form Example 96 (2 g, 5.99 mmole) in dioxane (10 ml) was treated with 0.26 g (6.5 mmole) of sodium hydroxide in 5 ml of water. After stirring for 16 h at 35° C., the reaction was worked up as described in Example 77 to give a 93% yield of product.

EXAMPLE 98

2(R,S)-[[(4-Morpholinyl)carbonyl]amino]-3,3-dimethyl-3-phenylpropionyl-His Amide of (2S,3R,4S) 1-(3-methylbutylcarbonylamino)-2,3-dihydroxy 4-amino-5-cyclohexylpentane.

Using the procedure of Example 78, but replacing Cbz-[(β,β-di-Me)-β-Ala]-Phe-OH with the product of Example 97 gave the desired product.

EXAMPLE 99

Cbz D-Ala-Phe-His Amide of (2S,3R,4S)-1-(3-Methylbutylcarbonylamino)-2,3-dihydroxy 4-amino 5-cyclohexylpentane Using the procedure of Example 78, but replacing the compound of Example 77 with Cbz-D-Ala-Phe gave the desired compound.

EXAMPLE 100

H-D Ala-Phe-His Amide of (2S,3R,4S)-1-(3-Methylbutylcarbonylamino)-2,3-dihydroxy-4-amino-5-cyclohexylpentane Using the procedure of Example 9, but replacing the resultant compound of Example 8 with the resultant compound of Example 99 gave the desired product.

EXAMPLE 101

Cbz-Sar-Phe-His Amide of (2S,3R,4S)-1-(3-Methylbutylcarbonylamino)-2,3-dihydroxy-4-amino-5-cyclohexylpentane.

Using the procedure of Example 78 but replacing the compound of Example 77 with Cbz-Sar-Phe gave the desired compound.

EXAMPLE 102

H-Sar-Phe-His Amide of (2S,3R,4S)-1 (3-Methylbutylcarbonylamino)-2,3-dihydroxy-4-amino-5-cyclohexylpentane.

Using the procedure of Example 9, but replacing the resultant compound of Example 8 with the resultant compound of Example 101 gave the desired product.

EXAMPLE 103

(N-Butyl, 4-OCH$_3$)-Phenylalanine

To a stirred 0° C. suspension of (4-OCH$_3$) phenylalanine (1.00 g, 5.12 mmol) and butyraldehyde (0.406 g, 110M %) in methanol (10 ml) was added sodium cyanoborohydride (241 mg, 75M %). The mixture was warmed to room temperature for 23 h and filtered. The solid was washed with methanol and suction dried to give (83% of the desired product. Mass spectrum: M+ = 251.

Anal. calcd. for $C_{14}H_{21}NO_3 \cdot \frac{1}{8}H_2O$ C, 65.3; H, 8.5; N, 5.4.

Found: C, 65.1; H, 8.3; N, 5.6

EXAMPLE 104

(N-Butyl, 4-OCH$_3$)-Phe-His Amide of (2S,3R,4S)-1-(3-Methylbutylcarbonylamino)-2,3-dihydroxy-4-amino-5-cyclohexylpentane.

Using the procedure of Example 78, but replacing the compound of Example 77 with the resultant product of Example 103 gave the desired compound.

EXAMPLE 105

Cbz-Isonipecotyl-Phe-His Amide of (2S,3R,4S)-1-(3-Methylbutylcarbonylamino)-2,3-dihydroxy-4-amino-5-cyclohexylpentane Using the procedure of Example 78, but replacing the resultant compound of Example 77 with Cbz Isonipectoyl-Phe gave the desired compound.

EXAMPLE 106

H-Isonipecotyl-Phe-His Amide of (2S,3R,4S) 1 (3-Methylbutylcarbonylamino)-2,3-dihydroxy-4-amino-5-cyclohexylpentane Using the procedure of Example 9, but replacing the resultant compound of Example 8 with the resultant compound of Example 105 gave the desired product.

EXAMPLE 107

(Pyrazin 2-yl carbonyl)-Phe-His Amide of (2S,3R,4S)-1-(3-Methylbutylcarbonylamino)-2,3-dihydroxy-4-amino-5-cyclohexylpentane Using the procedure of Example 78, but replacing the resultant product of Example 77 with (pyrazin-2-yl carbonyl)-Phe gave the desired product.

EXAMPLE 108

(Imidazol 4-yl-acetyl)-Phe-His Amide of (2S,3R,4S) 1-(3-Methylbutylcarbonylamino)-2,3-dihydroxy-4-amino-5-cyclohexylpentane Using the procedure of Example 78, but replacing the resultant product of Example 77 with (Imidazol 4-yl-acetyl) Phe gave the desired product.

EXAMPLE 109

Allyloxycarbonyl-Phe Leu Amide of (2S,3R,4S)-1-(3-Methylbutylcarbonylamino)-2,3-dihydroxy-4-amino-5-cyclohexylpentane.

Using the procedure of Example 33 but replacing Boc-Phe-Ala with allyloxy carbonyl-Phe-Leu and the product of Example 8 with that of 10, provided the desired product.

EXAMPLE 110

3-Hydroxypropyloxycarbonyl-Phe-Leu Amide of (2S,3R,4S)-1-(3-Methylbutylcarbonylamino)-2,3-dihydroxy-4-amino-5-cyclohexylpentane To a stirred 0° C. solution of the resultant compound of Example 109 (2.13 mmol) in dry tetrahydrofuran (THF, 50 ml) was added 9-borabicyclo[3.3.1]-nonane (9-BBN, 25.5 ml of a 0.5M solution in THF). The mixture was warmed to room temperature for 12 h and then cooled to 0° C. Water (15 ml) and 3M NaOH (4.5 ml)

were added followed 2 min later by 30% H₂O₂ (5 ml). The mixture was partitioned between brine (20 ml) and ethyl acetate (100 ml). The organic phase was washed (brine), dried (Na₂SO₄), filtered and evaporated to a thick oil. Recrystallization twice provided the desired compound.

EXAMPLE 111

Cbz-Gly Ester of the Resultant Compound of Example 110 (at 3 Hydroxypropyloxy Group).

To a stirred 0° C. suspension of the resultant compound of Example 110 (0.099 mol), Cbz-Gly-OH (20.7 mg, 0.099 mmol), and 4 dimethylamminopyridine (60 mg, 0.495 mmol) in dichloromethane (10 ml) was added ethyldimethylaminopropyl carbodiimide hydrochloride (38 mg, 0.198 mmol). The mixture was warmed at room temperature for 15 h and then diluted with dichloromethane and washed sequentially with 1M H₃PO₄, satd. NaHCO₃₃ and brine. Drying (Na2S04), filtering, and evaporating provided the desired compound.

EXAMPLE 112

H-Gly-Ester of the Resultant Compound of Example 110 (at 3-Hydroxypropyloxy Group)

The resultant compound of Example 111 (0.016 mmol) was hydrogenated (1 atmosphere H₂) with 10% Pd/C (4 mg) in methanol for 3 h. Filtration, evaporation and chromatography on silica (dichloromethane/methanol, 95/5-90/10) provided the desired product.

EXAMPLE 113

Lysine Ester of the Resultant Compound of Example 110 (at 3-Hydroxypropyloxy Group) Diacetic Acid Salt.

Following the procedure of Example 111 but replacing Cbz Gly-OH with a,e-di-Cbz-Lys-OH provided the desired protected peptide. Hydrogenation according to the procedure of Example 112, but replacing methanol with acetic acid provided the desired compound.

EXAMPLE 114

Hemisuccinate Ester of the Resultant Compound of Example 110 (at 3-Hydroxypropyloxy Group).

Using the procedure of Example 111, but replacing Cbz-Gly with benzyl succinate provided the protected product. Deprotection was achieved by following the procedure of Example 9 to give the desired product.

EXAMPLE 115

Phosphate Ester of the Resultant Compound of Example 110 (at 3-Hydroxypropyloxy Group).

Using the procedure of Example 111, but replacing Cbz Gly with dibenzyl- phosphate provided the protected product. Deprotection was achieved by following the procedure of Example 9 to give the desired product.

EXAMPLE 116

Boc-Phe-(N-methyl)His(im Boc) Amide of (2S,3R,4S)-1-(3-Methylbutylcarbonylamino)-2,3-dihydroxy-4-amino-5-cyclohexylpentane Following the procedure of Example 14, but replacing Boc Phe-His with Boc-Phe-(N-methyl)His(im-Boc) (Hoover, D. in U.S. Pat. No. 4,599,198), provided the desired product.

EXAMPLE 117

Boc Phe-(N-methyl)His Amide of (2S,3R,4S) 1 (3-Methylbutylcarbonylamino)-2,3-dihydroxy-4-amino-5-cyclohexylpentane The resultant compound of Example 116 was dissolved in THF/H₂O/acetic acid (1/⅓). After 10 h, the mixture was evaporated and the residue was partitioned between saturated aqueous NaHCO₃ and ethyl acetate. The organic layer was dried (Na₂SO₄), filtered, and evaporated to give the desired compound.

EXAMPLE 118

Benzoylleucine Methyl Ester.

Prepared from L-leucine methyl ester HCl and benzoyl chloride according to the procedure from Example 10.

EXAMPLE 119

2-Pyridylacetylleucine Methyl Ester.

Prepared from L-leucine methyl ester HCl and 2-pyridylacetic acid according to the procedure from Example 14.

EXAMPLE 120

Benzoylleucine.

Prepared from the resultant compound of Example 118 according to the procedure from Example 13. NMR (300 MHz, CDCl₃, ppm): 0.98 (d, 3H), 1.01 (d, 3H), 4.77 (m, 1H).

EXAMPLE 121

2-Pyridylacetylleucine.

Prepared from the resultant compound of Example 119 according to the procedure from Example 13.
Anal. calcd. for $C_{13}H_{18}N_2O_3.15H_2O$: C, 61.92; H, 7.27; N, 11.12.
Found: C, 61.72; H, 7.29; N, 11.07.

EXAMPLE 122

(2S,3R,4S)-1 (Benzoxylleucylamino)-2,3-dihydroxy-4-tert-butyloxycarbonylamino-5-cyclohexylpentane Prepared from the resultant compounds of Example 9 and Example 120 according to the procedure from Example 14.

EXAMPLE 123

(2S,3R,4S)-1-(2-Pyridylacetylleucylamino)-2,3-dihydroxy-4-tert-butyloxycarbonylamino-5-cyclohexylpentane.

Prepared from the resultant compounds of Example 9 and Example 121 according to the procedure from Example 14.

EXAMPLE 124

Boc-Phe-His Amide of(2S,3R,4S)-1-(Benzoylleucylamino)-2,3-dihydroxy-4-amino-5-cyclohexylpentane Using the procedure of Example 14 with the resultant product of Example 122 provided the desired compound.
Analysis calculated for $C_{44}H_{63}N_7O_8$-1.5 H₂O: C, 62.53; H, 7.87; N, 11.60.

Found: C, 62.28; H, 7.60; N, 11.87.

EXAMPLE 125

Boc-Phe-His Amide of (2S,3R,4S)-1-(2-Pyridyl-acetylleucylamino)-2,3-dihydroxy-4-amino-5-cyclohexylpentane Using the procedure of Example 14 with the resultant product of Example 123 provided the desired compound.

Analysis calculated for $C_{44}H_{64}N_8O_8 \cdot 0.5\ H_2O$: C, 62.76; H, 7.78; N, 13.31.

Found: C, 62.54; H, 7.67; N, 12.95.

The compounds of the present invention can be used in the form of salts derived from inorganic or organic acids. These salts include but are not limited to the following: acetate, adipate, alginate, benzoate, aspartate, benzenesulfonate, bisulfate, butyrate, citrate, camphorate, camphorsulfonate, dodecylsulfate, cyclopentanepropionate, digluconate, ethanesulfonate, fumarate, glucoheptanoate, glycerophosphate, heptonate, hemisulfate, hexanoate, hydrochloride, hydrobromide, hydroiodide, 2-hydroxy-ethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Also, the basic nitrogen-containing groups can be quaternized with such agents as loweralkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides like benzyl and phenethyl bromides, and others. Water cr oil-soluble or dispersible products are thereby obtained.

The novel compounds of the present invention possess an excellent degree of activity and specificity in treating renin associated hypertension in a host. The ability of the compounds of the invention to inhibit human renal renin can be demonstrated in vitro by reacting a selected compound at varied concentrations with human renal renin, free from acid proteolytic activity, and with renin substrate (human angiotensinogen) at 37° C. and pH 6.0. At the end of the incubation, the amount of angiotensin I formed is measured by radioimmunoassay and the molar concentration required to cause 50% inhibition, expressed as the $IC_{50}$, is calculated. When tested in accordance with the foregoing procedure, the compounds of the invention demonstrated $IC_{50}$'s in the range of $10^{-5}$ to $10^{-10}$ M as seen in Table I.

TABLE I

| Example Number | $IC_{50}$ (nM) |
| --- | --- |
| 14 | 4 |
| 15 | 6 |
| 16 | 10 |
| 17 | 0.4 |
| 19 | 0.65 |
| 20 | 10 |
| 24 | 20 |
| 25 | 3 |
| 31 | 55 |
| 32 | 50 |
| 36B | 10 |
| 36A | 30 |
| 47 | 2 |
| 50 | 1.5 |
| 52 | 4 |
| 69 | 10 |
| 70 | 1 |
| 71 | 5 |
| 72 | 4 |

Total daily dose administered to a host in single or divided doses may be in amounts, for example, from 0.001 to 10 mg/kg body weight daily and more usually 0.01 to 1 mg. Dosage unit compositions may contain such amounts of submultiples thereof to make up the daily dose.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination, and the severity of the particular disease undergoing therapy.

The compounds of the present invention may be administered orally, parenterally, by inhalation spray, rectally, or topically in dosage unit formulations containing conventional nontoxic pharmaceutically acceptable carriers, adjuvants, and vehicles as desired. The term parenteral as used herein includes subcutaneous injections, intravenous, intramuscular, intrasternal injection, or infusion techniques.

Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Suppositories for rectal administration of the drug can be prepared by mixing the drug with a suitable nonirritating excipient such as cocoa butter and polyethylene glycols which are solid at ordinary temperatures but liquid at the rectal temperature and will therefore melt in the rectum and release the drug.

Solid dosage forms for oral administration may include capsules, tablets, pills, powders, and granules. In such solid dosage forms, the active compound may be admixed with at least one inert diluent such as sucrose lactose or starch. Such dosage forms may also comprise, as is normal practice, additional substances other than inert diluents, e.g., lubricating agents such as magnesium stearate. In the case of capsules, tablets, and pills, the dosage forms may also comprise buffering agents. Tablets and pills can additionally be prepared with enteric coatings.

Liquid dosage forms for oral administration may include pharmaceutically acceptable emulsions, syrups, solutions, suspensions, and elixirs containing inert diluents commonly used in the art, such as water. Such compositions may also comprise adjuvants, such as wetting agents, emulsifying and suspending agents, and sweetening, flavoring, and perfuming agents.

The foregoing is merely illustrative of the invention and is not intended to limit the invention to the disclosed compounds. Variations and changes which are obvious to one skilled in the art are intended to be within the scope and nature of the invention which are defined in the appended claims.

What is claimed is:

1. A compound of the formula:

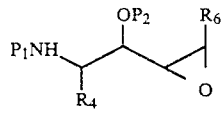

wherein $P_1$ is hydrogen or an N-protecting group; $P_2$ is hydrogen or an O-protecting group; $R_4$ is loweralkyl, $C_4$ to $C_7$ cycloalkylmethyl or benzyl; and $R_6$ is hydrogen or loweralkyl.

2. The compound of claim 1 wherein $P_1$ is hydrogen or an N-protecting group; $P_2$ is hydrogen or an O-protecting group; $R_4$ is $C_4$ to $C_7$ cycloalkylmethyl; and $R_6$ is hydrogen.

3. The compound of claim 1 wherein $P_1$ is tert-butoxycarbonyl or benzyloxycarbonyl and $P_2$ is tert-butyldimethylsilyl, trimethylsilyl, methoxymethyl, 2-methoxyethoxymethyl, benzyloxymethyl or benzyl.

4. A compound of the formula:

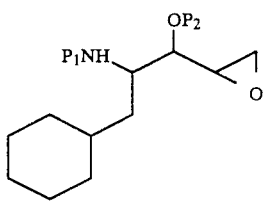

wherein $P_1$ is hydrogen or an N-protecting group and $P_2$ is hydrogen or an O-protecting group.

5. The compound of claim 4 wherein $P_1$ is tert-butoxycarbonyl or benzyloxycarbonyl and $P_2$ is tert-butyldimethylsilyl, trimethylsilyl, methoxymethyl, 2-methoxyethoxymethyl, benzyloxymethyl or benzyl.

6. A compound selected from the group consisting of 4-amino-5-cyclohexyl-3-hydroxy-1,2-oxopentane; 3-hydroxy-4-tert-butoxycarbonylamino-5-cyclohexyl-1,2-oxopentane; 3-tert-butyldimethylsilyloxy-4-tert-butoxycarbonyl-amino-5-cyclohexyl-1,2-oxopentane; and 3-tert-butyldimethylsilyloxy-4-benzyloxycarbonylamino-5-cyclohexyl-1,2-oxopentane.

* * * * *

UNITED STATES PATENT AND TRADEMARK OFFICE
CERTIFICATE OF CORRECTION

PATENT NO. : 4,977,277

DATED : DECEMBER 11, 1990

INVENTOR(S) : SAUL H. ROSENBERG; JAY R. LULY

It is certified that error appears in the above-identified patent and that said Letters Patent is hereby corrected as shown below:

On the title page, Column 1, line 1 change "FUNCTIONALIZED PEPTIDYL AMINODIOLS AND -TRIOLS 4-AMINO-5-CYCLOHEXYL-3-HYDROXY-1,2-OXOPENTANE AND DERIVATIVES THEREOF" to --4-AMINO-5-CYCLOHEXYL-3-HYDROXY-1,2-OXOPENTANE AND DERIVATIVES THEREOF--

On the title page, Column 2, line 19 change "(4-imidazoyl)methyl to --(4-imidazolyl)methyl--

Signed and Sealed this

Twenty-second Day of September, 1992

Attest:

DOUGLAS B. COMER

Attesting Officer        Acting Commissioner of Patents and Trademarks